United States Patent [19]
Swan et al.

[11] Patent Number: 5,563,056
[45] Date of Patent: Oct. 8, 1996

[54] PREPARATION OF CROSSLINKED MATRICES CONTAINING COVALENTLY IMMOBILIZED CHEMICAL SPECIES AND UNBOUND RELEASABLE CHEMICAL SPECIES

[75] Inventors: Dale G. Swan, St. Louis Park; Mark W. Josephson, Richfield; Melvin J. Swanson, Carver, all of Minn.

[73] Assignee: BSI Corporation, Eden Prairie, Minn.

[21] Appl. No.: 395,521

[22] Filed: Feb. 27, 1995

Related U.S. Application Data

[63] Continuation of Ser. No. 193,904, Feb. 9, 1994, abandoned, which is a continuation of Ser. No. 835,206, Feb. 13, 1992, abandoned.

[51] Int. Cl.⁶ .................. G12N 11/08; G01N 33/545; C07K 17/08; C07H 1/00
[52] U.S. Cl. .................. 435/180; 424/486; 435/178; 435/179; 435/181; 435/182; 436/529; 436/531; 436/532; 436/535; 530/402; 530/813; 530/815; 530/816; 530/817; 536/123.1; 536/124
[58] Field of Search .................. 435/177, 178, 435/179, 180, 181, 182; 436/529, 531, 532, 535; 530/815, 816, 402, 817, 813; 424/486; 536/123.1, 124

[56] References Cited

U.S. PATENT DOCUMENTS

| | | | |
|---|---|---|---|
| 3,959,078 | 5/1976 | Guire | 435/174 |
| 3,975,350 | 8/1976 | Hudgin et al. | 524/111 |
| 4,007,089 | 2/1977 | Smith, III | 435/180 |
| 4,716,122 | 12/1987 | Scheefers | 436/532 |
| 4,722,906 | 2/1988 | Guire | 436/501 |
| 4,979,959 | 12/1990 | Guire | 423/66 |
| 5,024,742 | 6/1991 | Nesburn et al. | 204/157.68 |

FOREIGN PATENT DOCUMENTS

| | | | |
|---|---|---|---|
| 04487 | 2/1990 | WIPO . | |
| WO9103990 | 5/1990 | WIPO . | |
| 9116425 | 10/1991 | WIPO | 435/181 |

OTHER PUBLICATIONS

Guire et al., *Stepwise Cross–Linking Reagents for Photocoupling of Enzymes and Lectins to Mammalian Cells,* Glycoconjugate Research II, pp. 1051–1054, (1979).

Guire et al., *Stepwise Thermophotochemical Cross–Linking for Enzyme Stabilization and Immobilization,* Enzyme Engineering 3, pp. 63–70 (1978).

Guire et al, *Photochemical Coupling of Enzymes to Mammalian Cells,* Pharmacological Research Communications, 9, No. 2, pp. 131–141 (1977).

*Primary Examiner*—David M. Naff
*Attorney, Agent, or Firm*—Fredrikson & Byron, P.A.

[57] ABSTRACT

A chemical specie is immobilized in a three dimensional, crosslinked matrix by bringing together in covalent bonding proximity a desired chemical specie and a polymeric coupling compound such as a photoderivatized polymer having at least two latent photochemical reactive groups per molecule, each latent reactive group being capable when activated of covalently bonding to another coupling compound molecule or to the chemical specie. The chemical specie may be a protein, carbohydrate, nucleic acid or lipid, and desirably is free of latent reactive groups that are activated upon activation of the latent reactive groups of the coupling compound. The latent reactive groups are simultaneously activated to cause formation via covalent bonding of a three-dimensional molecular network in which molecules of the chemical specie are covalently bonded to molecules of the coupling compound, and molecules of the coupling compound are covalently bonded to each other. The matrix containing the covalently bonded chemical specie may be contacted with a different chemical specie under conditions to incorporate the specie into the matrix in unbound form so that it can be gradually released from the matrix. In a preferred embodiment, the covelently bonded chemical specis is an antithrombic agent and the inbound chemical specil is an antibiotic. Preferably, the three dimensional matrix is formed as a coating upon a surface to which covalent bonds are formed upon activation of the latent reactive groups of the coupling compound.

12 Claims, No Drawings

PREPARATION OF CROSSLINKED MATRICES CONTAINING COVALENTLY IMMOBILIZED CHEMICAL SPECIES AND UNBOUND RELEASABLE CHEMICAL SPECIES

This application is a continuation of application Ser. No. 08/193,904, filed Feb. 9, 1994, which is a continuation of application Serial No. 07/835,206, filed Feb. 13, 1992, both now abandoned.

BACKGROUND OF THE INVENTION

It is often desirable to provide products such as catheters, blood bags, chromatography media, membranes, cell culture ware and the like with surfaced which have particular, predetermined characteristics. For example, it may be desirable to provide guide wires and catheters with external surfaces that permit them to slide easily within the vascular system of a human or other animal. It may be appropriate to provide the surfaces of prostheses that are to be implanted within the body with growth factors or similar chemical species that may contribute to the rapid proliferation of tissue on the prosthesis or, to the contrary, with chemical species for the purpose of prevention ongrowth of tissue. Some devices such as artificial eyes desirably have surfaces that are wettable and lubricious to the touch and that hence are comfortably received within the eyes socket. Poorly adherent surfaces, as of certain polymers, may be treated to improve adhesive characteristics. Blood bags and other tubes which may come into contact with blood may be treated with hemocompatible agents such as heparin or a heparin derivative. Bandages or other devices which come into contact with wounds may have surfaces that are provided with antibiotic materials. Various diagnostic tests may involve test protocols in which antibodies or antigens are covalently immobilized upon a surface.

U.S. Pat. No. 4,716,122 (Sheefers) refers to the use of a heterobifunctional photoactivatable compound, one functional group being an aryl azide and the other being an N-hydroxysuccinimide ester to bind an antibody or other protein to a solid surface.

A series of papers by Guire, et al describes the use of polyfunctional photoderivatives of glucose oxidase and catalase in association with concanavalin A and glucose oxidase, respectively: Guire et al, *Stepwise-Crosslinking Reagents for Photocoupling of Enzymes and Lectins to Mammalian Cells*, Glycoconjugate Research II, pp. 1051–1054, (1979); Guire et al, *Stepwise Thermophotochemical Crosslinking for Enzyme Stabilization and Immobilization*; Enzyme Engineering 3, pp. 63–70 (1978); and Guire et al, *Photochemical Coupling of Enzymes to Mammalian Cells*, Pharmacological Research Communications, 9, No. 2, pp 131–141 (1977).

U.S. Pat. No. 4,979,959 (Guire) refers to a biocompatible device in which various molecules such as cell attachment factors are covalently bonded to a solid surface through a chemical linking moiety.

International Application No. PCT/US88/04487 published Feb. 8, 1990 (Guire et al) refers to the bonding of various polymeric species to a solid surface through the use of latent reactive groups.

U.S. Pat. No. 3,959,078 (Guire) refers to the bonding of enzymes to a surface using a chemical linker employing an aryl azide photochemical group.

U.S. Pat. No. 4,007,089 (Smith III) teaches bonding a biologically active compound to a surface through a bifunctional linking compound by first attaching that compound to a surface via a phenyl azide group and then attaching the linking compound to the biologically active compound through an s-triazine group.

U.S. Pat. No. 5,024,742 (Nesburn et al) teaches a method of crosslinking collagen molecules to themselves or to other surfaces using a heterobifunctional reagent.

To covalently bond a specific chemical specie to a surface through photoactivation, a photoreactive group or other latent reactive group usually is first attached to the chemical specie and thereafter is activated to cause covalent bonding to the solid surface. Although procedures of this type have been quite successful, it has been necessary to manufacture latent reactive group-containing derivatives of each of the chemical species that one wishes to covalently bond to a surface. For example, heparin may be photoderivatized as taught in International Application No. PCT/US88/04487 published Feb. 8, 1990 and may be applied to various devices that come into contact with blood such as blood bags, tubes, and the like. However, the synthesis of latent reactive group-containing derivatives of various chemical species can be very expensive, both from the standpoint of developing the protocol for the synthesis of the derivative and also with respect to the manufacture of commercial quantities of the derivative.

It is also possible to attach desired chemicals to a surface by first providing the surface with latent reactive groups, then bringing the desired molecules into bonding association with the latent reactive groups, and activating the latent reactive groups to cause the formation of covalent bonds. Reference is made particularly to U.S. Pat. No. 4,722,906 (Guire). The method of this patent is dependent upon the ability of the target molecules to diffuse into bonding association with the latent reactive groups carried by the solid surface, however, and is highly selective of the target molecules that are to be attached.

BRIEF DESCRIPTION OF THE INVENTION

It has now been found that a wide variety of chemical species such as heparin, growth factors, natural and synthetic polymers and the like may be covalently immobilized in an insoluble, three dimensional, crosslinked matrix, preferably in solid or semi-solid form and most preferably in film form, utilizing a polymeric coupling compound having latent reactive groups. The invention avoids the necessity of synthesizing latent reactive group derivatives of the various chemical species, and provides a three dimensional matrix which exhibits properties of the chemical specie, the coupling compound or both. Speaking broadly, the method of the invention involves bringing together in covalent bonding proximity a desired chemical specie and a polymeric coupling compound having at least two latent reactive groups per molecule, each latent reactive group being capable of covalently bonding to another coupling compound molecule or to the chemical specie. The method involves simultaneously activating the latent reactive groups to cause formation via covalent bonding of a three-dimensional molecular network in which molecules of the chemical specie are covalently bonded to molecules of the coupling compound, and molecules of the coupling compound are covalently bonded to each other.

Preferably, a film comprising the coupling compound and the chemical specie is formed upon a surface, as by coating the surface with a solution containing the coupling compound and the chemical specie. In the most preferred embodiment, latent reactive groups carried by the polymeric coupling compound form covalent bonds to the surface, thereby co-immobilizing the coupling compound and the chemical specie to the surface. If desired, the surface may be a liquid surface or a surface to which the latent reactive groups do not readily form covalent bonds, and the completed film with its three dimensional, crosslinked structure may be removed from the surface for use elsewhere as, for example, a protective wound dressing.

Thus, in the preferred embodiment, the method of the invention involves forming on a surface a coating of the chemical specie that is desired together with and in covalent bonding proximity to a polymeric coupling compound having at least two latent reactive groups per molecule, each latent reactive group being capable of covalently bonding to a coupling compound molecule (either the same or different), to the chemical specie, or to the surface. The method involves simultaneously activating the latent reactive groups to cause formation via covalent bonding of a three-dimensional molecular network in which molecules of the chemical specie are covalently bonded to molecules of the coupling compound, and molecules of the coupling compound are covalently bonded to each other and to the surface.

The covalent bonds between the chemical specie and the coupling compound, between the coupling compound and the surface, and between different molecules of the coupling compound, form simultaneously, that is, during the same step. Thus, the chemical specie and the coupling compound are co-immobilized upon the surface. By judicious choice of the type and quantity of the coupling compound relative to the chemical specie, one may obtain three dimensional crosslinked networks of varying complexity and permeability.

The resulting three dimensional networks may be slightly or highly swellable in a solvent, but the networks remain insoluble. Free molecules of the chemical specie or another compound (that is, molecules that are not covalently bound to the coupling compound) may be incorporated into the three-dimensional network as desired.

The polymeric coupling compound contains an average of at least two latent reactive groups per molecule. Preferably, the average number of such groups per 100 Angstroms extended chain length ranges from 0.05 to 12 and preferably from 0.2 to 2. The coupling compound desirably is formed or derived from a synthetic polymer, although coupling compounds derived from natural polymers also may be employed.

DESCRIPTION OF THE PREFERRED EMBODIMENTS

The coupling compounds employed in the present invention are polymeric in nature; that is, they have repeating units and a molecular weight distribution. Most preferably, the coupling compounds are derived from or formed as synthetic polymers. The polymers of the invention include oligomers, homopolymers and copolymers resulting from addition or condensation polymerization, and natural polymers including nucleic acids, oligosaccharides, linear polysaccharides such as amylose, dextran, chitosan, heparin and hyaluronic acid, and branched polysaccharides such as amylopectin, glycogen and hemi-celluloses. The polymers may include several distinct polymer types, as may be prepared by terminal or side chain grafting. The polymers of the invention may include cellulose-based products such as hydroxyethyl cellulose, hydroxypropyl cellulose, carboxymethyl cellulose, nitrocellulose, cellulose acetate and cellulose butyrate, acrylics such as those polymerized from hydroxyethyl acrylate, hydroxyethyl methacrylate, glyceryl acrylate, glyceryl methacrylate, acrylic acid, methacrylic acid, acrylamide and methacrylamide, vinyls such as polyvinyl pyrrolidone and polyvinyl alcohol, nylons such as polycaprolactam, polylauryl lactam, polyhexamethylene adipamide and polyhexamethylene dodecanediamide, polyurethanes and polylactic acids, Of particular importance are the vinyl polymers such as polyvinyl pyrrolidone and polyacrylamide and the polyethers such as polyethylene glycol. For brevity, the invention is described below primarily with respect to the use of single coupling compounds that are homopolyfunctional (that is, that bear two or more identical latent reactive groups (and such is preferred)). However, one may employ a mixture of polymeric coupling compounds, if desired, and the coupling compounds themselves may be heteropolyfunctional (that is, they may contain two or more different latent reactive groups) and they may have different properties which they confer upon the matrix.

The polymeric coupling compounds employed in the invention desirably are soluble or at least dispersible in a solvent (to form, for example, a colloidal suspension), and preferably are soluble in water to at least the extent of 1 gram/l at 23° C. Moreover, the polymers of the invention desirably have extended chain lengths of at least about 45 Angstroms, and preferably at least about 1000 Angstroms.

"Extended Chain Length", as used herein, refers to theoretical straight line lengths measured along the backbone of a polymeric coupling compound, assuming that the polymer chain is stretched out to its maximum length consistant with observing proper bond angles between adjacent atoms. For example, polyethylene, —(CH$_2$—CH$_2$)—, exhibits an "extended" chain length between alternate carbon atoms of about 2.5 A (observing a bond angle of 109.5°), although the sum of the (carbon-carbon) bond distances along the molecule between alternate carbon atoms is about 3.06 A.

Latent reactive groups, broadly defined, are groups which respond to specific applied external stimuli to undergo active specie generation with resultant covalent bonding to an adjacent chemical structure, e.g., an adjacent same or different molecule. Latent reactive groups are those groups of atoms in a molecule which retain their covalent bonds unchanged under conditions of storage but which, upon activation by an external energy source, form covalent bonds with other molecules. The latent reactive groups generate active species such as free radicals and particularly nitrenes, carbenes, and excited states of ketones upon absorption of external electric, electromagnetic or kinetic (thermal) energy. Latent reactive groups may be chosen to be responsive to various portions of the electromagnetic spectrum, and latent reactive groups that are responsive to e.g., ultraviolet and visible portions of the spectrum are preferred and are referred to herein occasionally as "photochemical" groups. Latent reactive groups as described are generally well known.

The azides constitute a preferred class of latent reactive groups and include arylazides

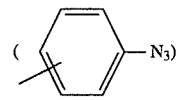

such as phenyl azide and particularly 4-fluoro-3-nitrophenyl azide, acyl azides

such as benzoyl azide and p-methylbenzoyl azide azido formates

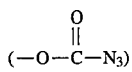

such as ethyl azidoformate, phenyl azidoformate, sulfonyl azides

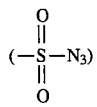

such as benzenesulfonyl azide, and phosphoryl azides

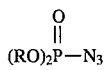

such as diphenyl phosphoryl azide and diethyl phosphoryl azide. Diazo compounds constitute another class of latent reactive groups and include diazoalkanes (—CHN$_2$) such as diazomethane and diphenyldiazomethane, diazoketones

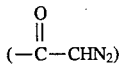

such as diazoacetophenone and 1-trifluoromethyl-1-diazo-2-pentanone, diazoacetates

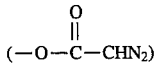

such as t-butyl diazoacetate and phenyl diazoacetate, and beta-keto-alpha-diazoacetates

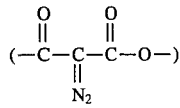

such as t-butyl alpha diazoacetoacetate. Other latent reactive groups include the aliphatic azo compounds such as azobiscyanovaleric acid, the diazirines

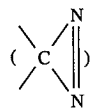

such as 3-trifluoromethyl-3-phenyldiazirine, and the ketenes (—CH=C=O) such as ketene and diphenylketene. Photoactivatable aryl ketones such as benzophenone and acetophenone are of particular importance inasmuch as these groups are subject to multiple reactivation in water and hence provide increased coupling efficiency. Peroxy compounds are contemplated as another class of latent reactive groups and include dialkyl peroxides such as di-t-butyl peroxide and dicyclohexyl peroxide and diacyl peroxides such as dibenzoyl peroxide and diacetyl peroxide and peroxyesters such as ethyl peroxybenzoate.

Upon activation of the latent reactive groups, the coupling compounds are covalently bound to coupling compound molecules and to chemical species (and, in the preferred embodiment, to the surfaces to which the chemical species are to be co-immobilized), by covalent bonds through residues of the latent reactive groups. Exemplary latent reactive groups, and their residues upon activation, are as follows:

| Latent Reactive Group | Residue Functionality | |
|---|---|---|
| aryl azides | amine | R—NH—R' |
| acyl azides | amide | R—C—NH—R' |
| azidoformates | carbamate | R—O—C—NH—R' |
| sulfonyl azides | sulfonamide | R—S—NH—R' |
| phosphoryl azides | phosphoramide | (RO)$_2$P—NH—R' |
| diazoalkanes | new C—C bond | |
| diazoketones | new C—C bond & ketone | |
| diazoacetates | new C—C bond & ester | |
| beta-keto-alpha-diazoacetates | new C—C bond & B-ketoester | |
| aliphatic azo | new C—C bond | |
| diazirines | new C—C bond | |
| ketenes | new C—C bond | |
| photoactivated ketones | new C—C bond & alcohol | |
| dialkyl peroxides | ethers | |
| diacyl peroxides | esters & new C—C bonds | |
| peroxyesters | ethers, esters, and new C—C bonds | |

The coupling compounds of the invention desirably have an average of at least two and preferably three or more latent reactive groups per molecule. Three-dimensional molecular networks may be formed through the use of polymeric coupling compound molecules each having two or more latent reactive groups, and in general the density of covalent bonds resulting from activation of the reactive groups and hence the "tightness" of the three-dimensional molecular network that is formed will be increased by decreasing the distance between latent reactive groups that are employed in the coupler compound.

Depending upon the method of fabrication of the polymeric coupling compound, that compound may contain varying numbers of latent reactive groups. A bifunctional polymeric coupling compound may have one latent reactive group at each of its two ends. For example, 4-bromomethylbenzophenone (derived from the free radical bromination of 4-methylbenzophenone) may be reacted with polyethylene glycol to form a bifunctional coupling compound having —(CH$_2$—CH$_2$—O)— repeating units and terminating in benzophenone latent reactive groups.

Polymeric coupling compounds used in the invention may have latent reactive groups incorporated at random positions along the polymer backbone. It may in some instances be desirable to provide polymers with more predictable sites for attachment of latent reactive groups, as described further below. Polymeric coupling compounds desirably, but not necessarily, have latent reactive groups at their ends or at random locations along their backbones (spaced from their ends) or both. By "backbone" as used herein in connection with polymer molecules, reference is made to the chain of atoms that is characteristic of the polymer and that results from the polymerization reaction. For example, polyethylene glycol polymers are characterized by a "backbone" of repeating —(—CH$_2$—CH$_2$—O—)— groups, whereas polyacrylamide and polyvinyl pyrrolidone have backbones characterized by carbon-carbon bonds, alternating carbon atoms in the backbone having pendent amide or pyrrolidone groups, respectively.

A polymer that includes at least one latent reactive group along its backbone spaced from its ends can be prepared by copolymerizing the basic monomer or monomers for the polymer with a monomer to which can be readily attached a latent reactive group such as a photoreactive group. For example, a photoreactive polyacrylamide polymer can be obtained by copolymerizing acrylamide with a small quantity of N-(3-aminopropyl)methacrylamide to provide random amine-functional groups along the polymer backbone, and then reacting the polymer with an amine-reactive photoreactive reagent such as benzoylbenzoylchloride. Coupling compounds may be derived from naturally occurring polymers such as hyaluronic acid by known methods such as those taught in U.S. Pat. No. 5,002,582, the teachings of which are incorporated herein by reference. The polymeric coupling compounds employed in the present invention desirably carry a sufficient number of latent reactive groups so that the average number of latent reactive groups per 100 Angstrom extended chain length ranges from 0.05 to 12 and preferably from 0.2 to 2.

The chemical species which can be co-immobilized together with the coupling compound in a three dimensional network according to the invention may be chosen from a wide variety of suitable substances. The chemical species used herein preferably are free of latent reactive groups of the type carried by the coupling compounds, that is, latent reactive groups that are activated upon activation of the latent reactive groups of the coupling compounds during the activation step. If desired, two or more chemical species may be employed, each lending to the matrix its particular properties. For example, it may be desired to immobilize at the same time an anticoagulant such as heparin, a thrombolytic agent such as streptokinase and, if desired, a protease inhibitor.

Some chemical species and the desired properties that these species exhibit when co-immobilized upon a surface are exemplified in the following non-limiting list:

| CHEMICAL SPECIES | FUNCTIONAL ACTIVITY |
|---|---|
| Synthetic Polymers | |
| Sulfonic acid-substituted polyacrylamide | Lubricity, negatively charged surface |
| Polyacrylamide | Lubricity, protein repulsion |
| Polyethylene glycol | Lubricity, cell and protein repulsion |
| Polyethyleneimine | Positively charged surface |
| Polylactic acid | Negatively charged surface |
| Polyvinyl alcohol | Lubricity |
| Polyvinyl pyrrolidone | Lubricity |
| Quaternary amine-substituted polyacrylamide | Lubricity, positively charged surface |
| Silicones | Lubricity |
| Conductive polymers (e.g., polyvinylpyridine, polyacetylene, polypyrrole | Electric conductivity |
| Carbohydrates | |
| Alginic acid | Lubricity, hydrophilicity |
| Cellulose | Lubricity, hydrophilicity, biodegradable glucose source |
| Chitosan | Positively charged surface, hydrophilicity |
| Glycogen | Hydrophilicity, biodegradable glucose source |
| Heparin | Antithrombogenicity, hydrophilicity, cell attachment |
| Hyaluronic acid | Lubricity, negatively charged surface |
| Pectin | Lubricity, hydrophilicity |
| Mono-, di- saccharides | Hydrophilicity |
| Dextran sulfate | Chromatography media |
| Proteins | |
| Antibodies | Antigen binding |
| Antithrombotic agents, e.g., Antithrombin III | Antithrombogenic surface |
| Albumin | Nonthrombogenic surface |
| Attachment proteins/peptides | Cell attachment |
| Enzymes | Catalytic surfaces |
| Extracellular matrix proteins/peptides | Cell attachment and growth |
| Growth factors, proteins/peptides | Cell growth |
| Hirudin | Antithrombogenic surface |
| Thrombolytic proteins (e.g., streptokinase, plasmin) | Thrombolytic activity |
| Lipids | |
| Fatty acids | Hydrophobicity, biocompatibility |
| Mono-, di- and triglycerides | Hydrophobicity, lubricity, biodegradable fatty acid source |
| Phospholipids | Hydrophobicity, lubricity, biodegradable fatty acid source |
| Prostaglandins/leukotrienes | Nonthrombogenic surface/ immobilized messengers |
| Nucleic Acids | |
| DNA | Substrate for nucleases/ affinity binding |
| RNA | Substrate for nucleases/ affinity binding |
| Nucleosides, nucleotides | Source of purines, pyrimidines, enzyme cofactors |
| Drugs/vitamins/cofactors | |
| Enzyme cofactors | Immobilized enzymes |
| Heme compounds | Globin binding/surface oxygenation |
| Drugs | Drug activity |
| Non-polymeric Materials | |
| Dyes (e.g., azo dyestuffs) | Coloring agents |
| Fluorescent compounds (e.g., fluorescein) | Fluorescence |

The product that is formed via activation of the latent reactive groups carried by the coupling compound is an insoluble, three dimensional crosslinked matrix that is desirably in solid or at least semi-solid (e.g., gel) form and that exhibits the properties of the chemical specie(s) incorporated in it, or properties of the coupling compound(s), or both. The coupling compound may be a polymer that itself provides the matrix with valuable properties; for example, use of a photo-derivatized polyvinylpyrrolidone may confer slipperiness and water wettability to the matrix. Both the coupling compound and the chemical specie may provide the matrix with desired properties. For example, a matrix formed from photopolyacrylamide as the polymeric coupling compound and heparin as the chemical specie may exhibit a reduction in protein absorption characteristic of the polyacrylamide and the antithrombogenic activity characteristic of heparin.

The matrices may be in the form of fibers, beads or other particles (for use, for example, in chromatographic columns), or in the form of free-flowing or non-flowing gels. However, the matrices preferably are in the form of films which may be continuous or discontinuous and which may have thicknesses ranging from a few nanometers up to a millimeter or more. A film may be self supporting, as when in sheet or tubing form; it may be in the form of a coating formed on and supported by a surface and in its most preferred form covalently bonded to the surface.

The crosslink density of the three-dimensional polymeric network that is formed can be varied as desired by judicious choice of the type and the amount of the coupling compound. For example, the use of polymeric coupling compounds that contain relatively few latent reactive groups will result in fewer covalent bonds being formed per unit length measured along the extended backbone of the polymer or per unit of molecular weight of the polymer, and the resulting three-dimensional network will be more open; that is, it will have a larger effective pore size. The use of polymeric coupling compounds having a greater number of latent reactive groups, or, for that matter, having latent reactive groups concentrated along a certain portion of the molecule, will provide a more tightly crosslinked, dense three-dimensional matrix.

The tightness of the three-dimensional network that is formed will depend upon the density of covalent bonds formed from the latent reactive groups carried by the coupling compound and this, in turn, depends upon the number of latent reactive groups per molecule of the coupling compound and the relative amounts of coupling compound and chemical specie that are employed. Of course, the ability of the polymeric coupling compound to become extended in solution (in contrast to assuming a tightly coiled configuration) also contributes to the loftiness or openness of the three dimensional network, and polymeric coupling compounds that are soluble to the extent of at least about 1 g/l in water are preferred.

The three-dimensional network that is formed in accordance with the method of the invention not only has utility in providing the resulting film with characteristics of the co-immobilized chemical specie, but also has utility in that it can be used to capture free chemical species (chemical species not covalently bound to a coupling compound molecule) so that the matrix, when in contact with a suitable liquid medium such as an aqueous solution, may gradually release the free chemical specie into the medium. The quantity of chemical specie that is thus released by the three-dimensional polymer network and the rate of release may depend upon a number of factors, including the loftiness or openness of the three-dimensional network, the amount of the free chemical specie that is employed, and the degree of affinity or repulsion between the three-dimensional network and the chemical specie.

In a preferred embodiment, the polymeric coupling compound and the chemical specie exhibit an affinity permitting them in solution to assume a preferred orientation with respect to each other prior to activation of the latent reactive groups, thereby facilitating covalent bonding therebetween when the latent reactive groups are activated. The affinity of the coupling compound and the chemical specie may involve the hydrophobic or hydrophilic characteristics of these compounds, e.g., in which hydrophobic portions of these compounds preferentially orient next to each other. The affinity between the coupling compound and the chemical specie may involve ionic attraction between portions of the molecules. For example, the polymeric coupling compound may be polyionic and the chemical specie also may be ionic, the coupling compound having a net charge opposite the net charge of the chemical specie. The coupling compound may be a vinyl copolymer containing aminopropyl pendent groups resulting from the use of an aminopropylmethacrylate monomer, the coupling compound thus having a net positive charge. The chemical specie may be a dextran sulfate having a net negative charge. In this embodiment, prior to the step of activating the latent reactive groups, the coupling compound and the chemical specie are brought into association permitting ionic attraction between them to pre-orient the chemical specie and the polymeric coupling compound with respect to each other before they are covalently bonded. Desirably, the polyionic coupling compound and the ionic chemical specie are provided in solution together to facilitate ionic attraction between them.

Free chemical species may be positioned or entrapped within the three-dimensional network that is formed by being present during formation of the network or by being added after the network has been formed. By employing a large amount of the chemical specie in comparison to the coupling compound, one may ensure that at least some of the chemical specie will not become covalently bound to the coupler, and the resulting free chemical specie may thus become physically entrapped within the network, and some may be slowly released.

If substantially all of the chemical specie becomes involved via covalent bonding within the three-dimensional network, additional chemical specie may be incorporated in the network by replacing the solvent that is present in the network with a solvent solution containing the chemical species. For example, solvent may be removed from a film that is initially formed, and the dried film may then be contacted with a solution of an additional quantity of the same or a different chemical species, causing molecules of the chemical species to enter the network and to become trapped therein upon removal of the solvent in a subsequent drying procedure. The resulting films, when placed in contact with a liquid medium such as blood or an open wound containing serous fluid, will release molecules of the free chemical species into the blood or serous fluid, the amount and rapidity of the release of the chemical agent depending upon how readily the chemical species can migrate from the coating into the blood or serous fluid, and, of course, upon the concentration gradients of the chemical species that are established. The remaining film, however, will yet retain molecules of the chemical species covalently bonded to it such that it will continue to itself exhibit characteristics of the chemical species. For example, heparin may be co-immobilized with a photoderivatized polyacrylamide coupling compound upon a surface, the process making use of a large amount of heparin so that some of the heparin is not covalently bonded to the polyacrylamide. The resulting film, when brought into contact with blood, releases heparin into the blood at a decreasing rate over a period of time. Once all of the available free heparin has escaped from the surface of the film into the blood, the heparin molecules that are covalently bound to the surface will continue to provide the surface with the antithrombogenic characteristics of heparin.

If desired, the three-dimensional network that is formed may be chosen to be subject to destruction in use. For example, the network may include ester linkages that are cleavable by the esterases in blood issuing from a wound. For example, a protective coating may be made from a vinyl polymer coupling compound containing aminoethylmethacrylate mer units to which latent reactive groups are coupled and a biologically active chemical species such as heparin. The coating may slowly degrade when in contact with blood due to hydrolysis of the ester bonds by esterases in the blood. In this manner, chemical species containing heparin and having the antithrombogenic properties of heparin may be slowly released.

If desired, free molecules of other chemical species (that is, molecules not covalently bound to the coupling compound) can be incorporated in the three-dimensional matrix. For example, as taught in greater detail below, photopolyacrylamide and heparin may be co-immobilized on a surface, and an antibiotic such as cephalosporin or vancomycin may be incorporated in the matrix. Upon contact with blood, the antibiotic is released gradually by being leached from the surface, leaving behind a heparinized surface. Different free molecules of various chemical species may be incorporated in a single matrix in this manner. For example, several antibiotics may be employed which exhibit activity against different microorganisms, or which provide more effective control over a single microorganism. If it is desired to form the film upon a surface to which the film is covalently bonded as it is formed, then the latent reactive groups that are employed are preferably attracted to the surface to be coated so that the latent reactive groups will readily come into covalent bonding proximity with the surface. Photochemical groups such as the aryl azides and the aromatic ketones commonly are relatively hydrophobic, as are many of the solid surfaces (e.g., polystyrene, polysulfone and polyolefin) that may be coated in accordance with the invention. "Hydrophilic" and "hydrophobic" are used herein to describe compositions broadly, as water loving and water hating, respectively, in line with the following observations: Hydrophilic compounds are usually relatively polar and often are ionizable. Such compounds usually bind water molecules strongly. Hydrophobic compounds are usually relatively non-polar and non-ionizing. Hydrophobic surfaces will generally cause water molecules to structure in an ice-like conformation at or near the surface. "Hydrophobic" and "hydrophilic" are relative terms, of course, and are used herein in the sense that various compositions, liquids and surfaces may be hydrophobic or hydrophilic relative to one another. A discourse on the subject is found in Hoffman, *Letter to the Editor: A general classification scheme for "hydrophilic" and "hydrophobic" biomaterial surfaces*, J. Biol. Mat. Res. 20, pp. ix–xi (1986).

Crosslinked, three-dimensional matrix films of co-immobilized coupling compound and chemical species can be produced by combining the polymeric coupling compound and chemical species precursors in solution and then physically forming the solution into a sheet or film configuration before activating the latent reactive groups. For example, an aqueous solution of the precursors may be floated upon the surface of a non-miscible liquid such as a perfluorocarbon liquid. After activating the latent reactive groups of the polymeric coupling compound, the film, which may at this point be self-supporting, may be removed from the liquid surface. It is contemplated that this process may be performed on a continuous basis if desired, the precursor solution being sheeted onto a bath of the non-miscible liquid at one end of the bath, and the continuous self-supporting film being removed from the other end of the bath. The surface upon which the film is physically formed may be a solid surface such as polytetrafluoroethylene to which the latent reactive groups, when activated, do not readily bond and from which the film may be removed.

The method of the invention finds particular utility, however, in the formation of a film upon a surface, desirably a solid surface, to which the film becomes covalently bonded by latent reactive groups of the coupling compound. In this embodiment, the surface itself becomes chemically involved in the formation of the three-dimensional matrix. Such surfaces preferably have abstractable hydrogen atoms and participate readily in the formation of covalent bonds upon activation of the latent reactive groups.

In the preferred process of the invention, the coupling compound and the selected chemical specie (several coupling compounds or chemical species or both may be used) are applied to a surface, and the latent reactive groups of the coupling compounds are simultaneously reacted to form covalent bonds between the chemical specie and the coupling compound, between the coupling compound and the surface, and between different molecules of the coupling compound, to form a three dimensional molecular network. If desired, the coupling compound and the chemical specie may be combined and partially pre-reacted before they are applied to the surface.

To facilitate the co-immobilization process, the polymeric coupling compound and the chemical specie are applied to a surface from a solvent medium, preferably from solution and most preferably from aqueous solution. Preferably, the coupling compound and the chemical specie are combined in solution and applied as a wet film to the surface, following which the latent reactive groups are activated, by light, in the case of photoreactive groups. Solvent may be partially or totally removed from the wet film before activation of the latent reactive groups. Alternatively, the latent reactive groups may be reacted in the presence of the solvent. The coupling compound and the chemical specie may be applied to the surface as separate, wet films which blend or interdiffuse together to bring the coupling compound and the chemical specie into covalent bonding proximity, and it is contemplated that the first wet film may be at least partially dried before application of the second film.

Defined broadly, the "surface" upon which may be formed a film according to the invention is defined by the interface between distinct phases of compositions, the solid surface of a tangible object such as a sheet of material being perhaps the most commonly thought of surface and being defined by a gas-solid interface. Surfaces may be defined by the interface between liquid and solid compositions as exemplified by the solid surface of solid particles in suspension, by the interface between immiscible liquids as exemplified by emulsions, and by gas-liquid interfaces as exemplified by the surface of a liquid bath.

A solid surface as referred to herein is a tangible surface defined by the interface between solid phase materials (including soft gels) and gas or liquid phases. Specific examples include the surfaces of medical devices such as blood bags, catheters, bone and tissue prostheses, and living bone and tissue surfaces. Other solid surfaces are exemplified as the surfaces of membranes, fibers such as hollow fibers employed in chemical reactors and fibers employed in structural composites, and chromatographic media particles and the like.

The invention may be more easily understood by reference to the following illustrative, non-limiting examples:

EXAMPLE 1

Preparation of Bis(benzoylbenzyl) Polyethyleneglycol Ether (BBE-PEG(3350)-BBE)

To 100 g of polyethylene glycol 3350 (PEG(3350)) in a 1 liter round bottom flask was added 400 ml of toluene. The toluene was evaporated off to remove moisture. The PEG was then dissolved in tetrahydrofuran (250 ml) by stirring at reflux temperatures under an argon atmosphere, and the solution was allowed to cool. To the solution was added NaH (2.3 g) and the solution was stirred for an hour, after which 20.5 g of bromomethylbenzophenone was added. The cloudy mixture was stirred overnight. Ammonium chloride (10.2 g) and water (4 ml) were added and the mixture was stirred for 30 minutes. The solvent was evaporated off, and 150 ml of toluene was added and the cloudy solution was filtered to obtain a clear filtrate. The clear solution was then slowly added to 300 ml of ice cold diethyl ether to precipitate the polymer which was then collected by filtration, washed with ethyl ether and dried.

EXAMPLE 2

Preparation of Photoderivatized Polyacrylamide (Photo PAA)

Acrylamide (10.24 g) was dissolved in 200 ml of deionized water. To the solution was added 0.279 mg of N-(3-aminopropyl)methacrylamide, 0.33 g of ammonium persulfate and 0.155 g of N,N,N',N'-tetramethylethylenediamine. The solution was evacuated in a filter flask with a water aspirator for 10 minutes. The tubing was clamped and the solution left under vacuum for one hour. The resulting polymer solution was dialyzed against deionized water. To 150 ml of polymer solution in a PTFE bottle containing 3.0 g of polymer was added 0.504 ml of triethylamine. To this solution was added 30 ml of 28.4 mg/ml 4-benzoylbenzoyl-chloride in $CHCl_3$. The bottle was capped tightly and shaken for one hour. The bottle was then centrifuged for 10 minutes to separate the phases after which the aqueous layer was removed, dialyzed and lyophilized.

EXAMPLE 3

Co-immobilization of Polyvinylpyrrolidone 1.0 gm of polyvinylpyrrolidone (PVP) having a number average molecular weight of about 360,000 was dissolved in 25 ml of water. 350 mg of BBE-PEG(3350)-BBE prepared as in Example 1 were dissolved in 25 ml of water. The solutions were mixed and lyophilized. 100 mg samples were illuminated with ultraviolet light for 10 seconds and for 10 minutes, respectively, to achieve limited pre-reaction of the photoreactive groups carried by the photopolyethylene glycol. The dry mixtures were redissolved in water and diluted to give a solution that was 4.5 mg/ml in 30% isopropanol. 65 ul of these solutions were sprayed onto one side of a 1"×1" piece of polymethylmethacrylate (PMMA), and the coating was irradiated with ultraviolet light for 3 minutes. Both samples were readily wettable with water. After washing, the wet films were slippery when rubbed with the fingers (a characteristic of PVP but not of PMMA or photo PEG), indicating that the PVP had been bound to the surface.

EXAMPLE 4

Heparin Co-Immobilized Onto Regenerated Cellulose and Polysulfone Hollow Fiber Dialysis Membranes Heparin was dissolved at 3 mg/ml in an aqueous solution of photo PAA prepared as in Example 2 at 3 mg/ml for subsequent co-immobilization on membrane surfaces. Another aqueous solution was prepared by dissolving heparin at 6 mg/ml in photo PAA at 3 mg/ml. A photoreactive derivative of heparin (photoheparin) was prepared by reacting heparin with benzoyl-benzoyl-epsilon-aminocaproyl-N-oxysuccinimide in dimethylsulfoxide/carbonate buffer, pH 9.0. The solvent was evaporated and the photoheparin was dialyzed vs. water, and lyophilized, and then dissolved in water at 3 mg/ml. Heparin was also dissolved in water at 3 mg/ml for subsequent absorption onto membrane surfaces. Each solution was applied to specimens of regenerated cellulose membranes by soaking overnight at 37° C. The membranes were then dried and UV illuminated in a $N_2$ atmosphere for 2 minutes. The membranes were then washed four times for three minutes each in an ultrasonic bath of 0.5% Tween 20 in phosphate buffered saline (PBS) followed by the same washing procedure in deionized water. The membranes were further washed for 24 hours in 0.5% Tween 20 followed by a 24-hour wash in 1% bovine serum albumin (BSA). Heparin activity was then measured by a Factor Xa inhibition assay. The results are given below.

| Regenerated Cellulose Immobilization Condition | Heparin Activity (mU/cm$^2$) |
|---|---|
| Adsorbed heparin | 2.4 |
| Photo-heparin | 5.8 |
| Co-immobilized heparin (3 mg/ml) | 5.2 |
| Coimmobilized heparin (6 mg/ml) | 7.9 |

In a similar experiment, heparin at several concentrations was coimmobilized with photo-PAA as described above onto polysulfone hollow fiber membranes. After washing, the heparin activity was measured, yielding the following results:

| Heparin Concentration, mg/ml | Heparin Activity (mU/cm$^2$) |
|---|---|
| 6.0 | 8.4 ± 2.5 |
| 2.5 | 8.4 ± 1.9 |
| 1.0 | 7.2 ± 1.3 |
| 0.6 | 4.6 ± 1.4 |

EXAMPLE 5

Collagen Co-Immobilized Onto PTFE Membranes For Cell Culture

Photo PAA was prepared as follows:

To 2 grams of N-(3-aminopropyl)methacrylamide (APMA) in 80 ml of dry dimethylsulfoxide was added 4.96 gm of 4-benzoylbenzoyl-epsilon-aminocaproyl-N-oxysuccinimide and 2.26 ml of N,N,N'N'-tetramethylethylenediamine. The solution was stirred for four hours, after which 20 gm of acrylamide in 286 ml of DMSO and 300 mg of azobis(isobutyronitrile) in 100 ml of DMSO were added. The solution was bubbled with helium for 5 minutes, after which the space above the solution was filled with argon. Polymerization was allowed to occur at 55° C. for 24 hours. The polymer was then precipitated in ethanol, redissolved in 250 ml of deionized water, and dialyzed vs water. Insoluble material was removed by filtration, and the clear solution was lyophilized.

Polytetrafluoroethylene (PTFE) membranes were first prewetted with methanol and then were soaked for 4 hours in an aqueous solution (5 mg/ml) of the photo PAA prepared above. The coatings then were illuminated with UV light for 3 minutes and washed in PBS. Native bovine skin collagen (containing types I and III) at 1.25 mg/ml was dialyzed vs 3 mM HCl, and the photo PAA prepared as above was dissolved in the collagen solution at 5 mg/ml. Porous PTFE membranes that previously had been coated with photo PAA and irradiated were then soaked in the solution for 4 hours at 4° C. The membranes were illuminated with UV light for 3 minutes, after which they were washed extensively with PBS and air dried.

The collagen-coated membranes thus produced were tested in cell culture studies using both PA-1 (human, ovarian) and NRK (rat, kidney) cell lines and demonstrated good cell attachment and growth.

EXAMPLE 6

Co-Immobilization of Streptokinase

Polyethylene tubing was filled with a solution containing 2.5 mg/ml photo PAA prepared as in Example 5 and 2.5 mg/ml streptokinase, after which the tubing was UV illuminated for 8 minutes. After rinsing the tubing by circulating buffer through it for 24 hours, streptokinase activity was detected in the tubing by adding plasminogen (0.5 units/ml) and D-val-leu-lys-p-nitroanilide and measuring at 405 nm the color generated by release of p-nitroaniline.

EXAMPLE 7

Co-Immobilization of Photopolyacrylamide and Heparin to Polyvinylchloride Tubing Photopolyacrylamide prepared as in Example 3 was dissolved in water at 25 mg/ml. Sodium heparin was dissolved in water at 50 mg/ml. 20 ml of the photo PAA solution prepared as in Example 2 and 5 ml of the heparin solution were mixed to give 25 ml of co-immobilization solution containing 30 mg/ml of total solids. External surfaces of polyvinylchloride tubing were precleaned with an alcohol wipe followed by argon plasma treatment and then were dipped in the co-immobilization solution. Excess solution was drained away, the coating was air dried, and a second, identical coating application was performed. The tubing was exposed to UV light to cure the hydrogel-heparin matrix. Surface treatment of the polyvinylchloride by this two-coat process resulted in heparin activity levels of 3500 mU/cm$^2$ as measured by a thrombin inhibition assay. Long term exposure of these coated materials to albumin-containing phosphate-buffered saline (intended to simulate blood contact) gave significant release of soluble heparin and also resulted in immobilized heparin activities of approximately 10 mU/cm$^2$.

EXAMPLE 8

Co-Immobilization of Photo PAA and Heparin to a Surface with Subsequent Loading and Release of Antimicrobial Agents Photo PAA, as prepared in Example 2, and heparin are co-immobilized upon a surface as described in Example 7. After rinsing away the unbound heparin with water and subsequently drying the coating, the immobilized polyacrylamide-heparin matrix is placed overnight in an aqueous solution containing 100 mg/ml of vancomycin. The tubing is removed and air-dried. Upon subsequent blood contact with the tubing, the antibiotic is released from the photo PAA-heparin hydrogel at a gradually decreasing rate. Complete release of the matrix-adsorbed drug leaves a biocompatible heparinized, hydrogel surface.

EXAMPLE 9

Preparation of Co-Immobilized Photo PAA/Hyaluronic Acid Film

To 10 ml of a 10 mg/ml solution of hyaluronic acid in water was added 200 mg of the photo PAA prepared in Example 5. The viscous solution was spread onto a polytetrafluoroethylene (PTFE) textured surface, was allowed to dry, and was illuminated with ultraviolet light. The resulting film was removed from the PTFE surface as an intact film, the pattern of the textured PTFE being evident on the lower surface of the film. When wet with water, the film swelled but did not dissolve. A solution of hyaluronic acid alone was also spread on an identical film, dried and illuminated. The resulting film readily redissolved in water.

EXAMPLE 10

Polyethylene Glycol Co-Immobilization Onto Polycarbonate Membranes

The mono benzoylbenzyl ether of polyethylene glycol (BBE-PEG-OH) was synthesized using polyethylene glycol (HO-PEG-OH) by the following procedure: To polyethylene glycol (20 g, mol. wt. 8000) dissolved in 100 ml of dry tetrahydrofuran (THF) was added 60 mg of NaH followed by stirring under a positive $N_2$ pressure for 2 hours. 4-Bromomethylbenzophenone (344 mg) was added and the solution was stirred overnight under a positive $N_2$ pressure. The reaction was quenched by adding 267 mg of NH4Cl in 2 ml of water. The THF was evaporated off, then the polymer was dissolved in 100 ml of saturated NaCl solution. The solution was extracted twice with 100 ml of $CHCl_3$. The chloroform solution was dried over Na2SO$_4$. The solvent was evaporated and the resulting BBE-PEG-OH polymer was dissolved in and precipitated from toluene/ethyl ether.

A mixture of equal weights of BBE-PEG-OH, HO-PEG-OH and the BBE-PEG-BBE of Example 1 was dissolved at 0.5 mg/ml in a 50% isopropanol solution in water. Commercially available porous polycarbonate membranes were soaked in the resulting solution for 10 minutes and were dried in a cold air stream for 3 minutes. The membranes were exposed to UV radiation for 10 seconds, and then were washed in water for 15 minutes and air dried. The wettability of the membranes, as measured by the ease with which an aqueous solution passes through them, was tested by measuring the time required to pass 500 ml of water through 47 mm diameter discs under a pressure drop across the discs of 625 mm Hg. 14 Minutes were required for the discs prepared above, whereas 17 minutes were required for identical polycarbonate discs that were treated instead by soaking in a polyvinyl pyrrolidone solution. For comparison, water under this pressure differential will not pass through an uncoated polycarbonate disc.

EXAMPLE 11

Synthesis of Polyionic Polymeric Coupling Compound

To 85 mg of N-(3-aminopropyl)methacrylamide in 5 ml of dry dimethylsulfoxide was added 102 mg of benzoylbenzoyl-epsilon-aminocaproyl-N-oxysuccinimide and 40 ul of N,N,N'N'-tetramethylethylenediamine. The solution was stirred overnight, after which 1.0 gm of N-acryloyltris(hydroxymethyl)aminomethane in 5 ml of DMSO and 50 mg of azobis(isobutyronitrile) in 5 ml of DMSO were added. The solution was bubbled with nitrogen for 5 minutes, sealed and stored at 55° C. overnight. The resulting polymer was precipitated in ethanol, redissolved in 10 ml of deionized water, dialyzed vs water and lyophilized.

EXAMPLE 12

Coimmobilization of Dextran Sulfate Onto Polystyrene Beads For Purifying Clotting Factors From Blood The ionic polymer prepared in Example 11 and the photo PAA prepared as in Example 5 were each dissolved in deionized water at 5 mg/ml. To each solution dextran sulfate (average molecular weight of 500,000) was added at 10 mg/ml. These solutions were incubated with polystyrene beads (297–1000 um diameter) for 24 hours at room temperature with mixing. The beads were then filtered to remove coating solutions and air dried. The beads were then spread into thin layers on aluminum foil, illuminated with UV light for 1.5 minutes, shaken, and illuminated for an additional 1.5 minutes. The beads were then washed with deionized water and tested for ability to bind Azure A (which turns from blue to purple upon binding to a sulfated surface). By visual observation, both preparations of coated beads were significantly colored but the beads coated with dextran sulfate coimmobilized with the polyionic polymeric coupling compound were significantly more purple than the beads coated with dextran sulfate coimmobilized with the photo PAA, which is indicative of a higher concentration of dextran sulfate coimmobilized with the ionic coupling compound.

While a preferred embodiment of the present invention has been described, it should be understood that various changes, adaptations and modifications may be made therein without departing from the spirit of the invention and the scope of the appended claims.

What is claimed is:

1. Method for forming a matrix having a first chemical specie covalently immobilized therein and including free molecules of a second chemical specie different from the first chemical specie whereby the second chemical specie molecules may be gradually released from the matrix, comprising:

a. bringing together in covalent bonding proximity a first chemical specie and a polymeric coupling compound that is different than the first chemical specie having at least two photochemical latent reactive groups per molecule, each latent reactive group being capable of covalently bonding to another coupling compound or to the chemical specie;

b. simultaneously activating the latent reactive groups to cause formation via covalent bonding of a three-dimensional molecular network in which molecules of the chemical specie are covalently bonded to molecules of the coupling compound, and molecules of the coupling compound are covalently bonded to each other, and c. contacting the three dimensional network with a second chemical specie different from the first chemical specie under conditions favoring incorporation of the second chemical specie in said three dimensional network in unbound form so that the second chemical specie can be gradually released, wherein said first chemical specie and said second chemical specie are selected from the group consisting of carbohydrates, proteins, nucleic acids and lipids.

2. The method according to claim 1 wherein either the first or second chemical specie is a carbohydrate selected from the group consisting of chitosan, heparin, hyaluronic acid, alginic acid, cellulose, glycogen, pectin, and dextran sulfate.

3. The method according to claim 1 wherein either the first or second chemical specie is a carbohydrate selected from the group consisting of monosaccharides and disaccharides.

4. The method according to claim 1 wherein either the first or second chemical specie is a protein selected from the group consisting of antithrombic agents, attachment proteins, extracellular matrix proteins, growth factors and enzymes.

5. The method according to claim 1 wherein both the first and second chemical specie is a carbohydrate selected from the group consisting of chitosan, heparin, hyaluronic acid, alginic acid, cellulose, glycogen, pectin, and dextran sulfate or a protein selected from the group consisting of antithrombic agents, attachment proteins, extracellular matrix proteins, growth factors and enzymes.

6. The method of claim 1 wherein said first chemical specie is an antithrombic agent and said second chemical specie is an antibiotic.

7. The method of claim 1 wherein the coupling compound is selected from the group consisting of photoderivatized forms of the following polymers; polyacrylamide, polyethylene glycol, polyvinyl pyrrolidone, polyvinylpyridine, polyacetylene, and polypyrrole.

8. The method according to claim 7 wherein the coupling compound is a photoderivatized form of polyacrylamide.

9. The method according to claim 7 wherein the coupling compound is a photoderivatized form of polyethylene glycol.

10. The method according to claim 7 wherein the coupling compound is a photoderivatized form of polyvinyl pyrrolidone.

11. A matrix prepared according to the method of claim 1.

12. A method for forming a matrix having a first chemical specie covalently immobilized therein and including free molecules of a second chemical specie different from the first chemical specie whereby the second chemical specie molecules may be gradually released from the matrix, comprising:

a. bringing together in covalent bonding proximity a first chemical specie and a polymeric coupling compound that is different than the first chemical specie having at least two photochemical latent reactive groups per molecule, each latent reactive group being capable of covalently bonding to another coupling compound or to the chemical specie;

b. simultaneously activating the latent reactive groups to cause formation via covalent bonding of a three-dimensional molecular network in which molecules of the chemical specie are covalently bonded to molecules of the coupling compound, and molecules of the coupling compound are covalently bonded to each other, and c. contacting the three dimensional network with a second chemical specie different from the first chemical specie under conditions favoring incorporation of the second chemical specie in said three dimensional network in unbound form so that the second chemical specie can be gradually released, wherein the first and second chemical specie are each, independently, a carbohydrate selected from the group consisting of chitosan, heparin, hyaluronic acid, alginic acid, cellulose, glycogen, pectin and dextran sulfate or a protein selected from the group consisting of antithrombic agents, attachment proteins, extracellular matrix proteins, growth factors and enzymes, and the coupling compound is selected from the group consisting of photoderivatized forms of the following polymers: polyacrylamide, polyethylene glycol, polyvinyl pyrrolidone, polyvinylpyridine, polyacetylene, and polypyrrole.

* * * * *

UNITED STATES PATENT AND TRADEMARK OFFICE
CERTIFICATE OF CORRECTION

PATENT NO. : 5,563,056
DATED : October 8, 1996
INVENTOR(S) : Dale G. Swan, et al.

It is certified that error appears in the above-indentified patent and that said Letters Patent is hereby corrected as shown below:

Abstract, line 22, replace "covelently" with --covalently--.
Abstract, line 22, replace "specis" with --specie--.
Abstract, line 23, replace "specil" with --specie--.
Column 1, line 17, replace "surfaced" with --surfaces--.
Column 1, line 26, replace "prevention" with --preventing--.
Column 4, line 32, replace "consistant" with --consistent--.
Column 16, line 18, replace "NH4Cl" with --$NH_4Cl$--.
Column 16, line 22, replace "Na2SO$_4$" with --$Na_2SO_4$--.

Signed and Sealed this

Fourth Day of March, 1997

Attest:

BRUCE LEHMAN

*Attesting Officer*     *Commissioner of Patents and Trademarks*